United States Patent [19]

Shelden et al.

[11] Patent Number: 4,638,798

[45] Date of Patent: Jan. 27, 1987

[54] STEREOTACTIC METHOD AND APPARATUS FOR LOCATING AND TREATING OR REMOVING LESIONS

[76] Inventors: C. Hunter Shelden, 1345 Bedford Rd., San Marino, Calif. 91108; Gilbert D. McCann, 2247 No Villa Hts. Rd., Pasadena, Calif. 91107

[21] Appl. No.: 185,937

[22] Filed: Sep. 10, 1980

[51] Int. Cl.⁴ .............................................. A61B 17/00
[52] U.S. Cl. .................................. 128/303 B; 128/653
[58] Field of Search .................... 128/303 B, 653, 659, 128/660

[56] References Cited

U.S. PATENT DOCUMENTS 4,181,939  1/1980  Lyons .................................. 128/659

FOREIGN PATENT DOCUMENTS 1206116  12/1965  Fed. Rep. of Germany ... 128/303 B

*Primary Examiner*—Michael H. Thaler
*Attorney, Agent, or Firm*—Freilich, Hornbaker, Rosen & Fernandez

[57] ABSTRACT

A stereotactic method and apparatus for treating a region of a patient's body defines points in the region using a three-dimensional coordinate system with reference to a ring attached to the patient for establishing a reference point for the three-dimensional coordinate system at the center of the ring. The same ring and reference point is then used for stereotactically controlling instruments used to treat the region. The ring is preferably provided with pins extending parallel to the axis of the ring, and equidistant from the center, for precise location of the center and of a base-line scan for correlation between the location of the region to be treated and the control system for treatment of the region. Prior to treatment, a series of noninvasive tomography scans are made through the region and at least part of the pins for determining the coordinates of at least one point of the region selected for the treatment with respect to the center of the ring. All parameters of the system for stereotactic control of instruments used for treatment are then determined with respect to the ring center as a reference point.

9 Claims, 9 Drawing Figures

STEREOTACTIC METHOD AND APPARATUS FOR LOCATING AND TREATING OR REMOVING LESIONS

BACKGROUND OF THE INVENTION

This invention relates to a system (method and apparatus) for the location and treatment or removal of lesions, such as intracranial central nervous system (CNS) lesions, and more particularly for defining the location of lesions in a three-dimensional coordinate system with reference to a stereotactic guide ring used during surgery or treatment.

The integrated concept of the present invention has more general applications than the particular surgical procedure to be described for locating and removing a tumor in the brain. It may also be used for precisely locating adjuvant therapy. Also it can be used in other parts of the body for either surgical procedure or for adjuvant therapy. The system utilizes a stereotactic guide ring, as will be described by way of example for the removal of CNS lesions. There, as in other parts of the body, the removal could be carried out with a knife, a laser or concentrated gamma rays. Emphasis in the exemplary embodiment to removal of a CNS lesion is due only to the early success of the system for removing brain tumors.

In the past, the cure rate for malignant brain tumors has been virtually zero. This is partly due to the size to which the tumor must grow before its presence is diagnosed. If tumors can be detected while still very small in size, possibly 2 mm, they can be precisely located and removed by the surgical procedures described hereinafter. The amount of cancer material that might be left is so small that precisely administered adjuvant therapy, local irradiation, chemotherapy, immuno therapy, etc., may be satisfactory additional treatments.

The techniques that have been used for brain imaging in trying to determine the presence of a tumor are various. See Wm. H. Oldendorf, M.D., "The quest for an image of brain: A brief historial and technical review of brain imaging techniques," Neurology, 28:517–533, June, 1978. Of the various techniques, computerized tomography (CT) has a distinct advantage. Like other techniques, it is noninvasive, but unlike other techniques, it provides explicit two-dimensional images (sections) of the brain. To develop a three-dimensional image, it is necessary to provide a number of parallel CT scans (slices) over the volume of interest. CT scan instruments have been capable of imaging very accurately across 5-mm slices, and more recently across 1.7-mm slices. In other words, CT scanners have for some time been able to image very accurately thin cross sections of brain tissue in a two-dimensional (X-Y coordinate) display.

By using specially designed computer programs to analyze the digitized CT scan data, it should be possible to determine within a fraction of a millimeter the depth (Z coordinate) from the top of the head at which the tumor is located as well as the side-to-side (X coordinate) and front-to-back (Y coordinate) positions. The problem is how to use this information to locate the tumor with the same degree of accuracy during surgery as is possible in the CT scan. In the past, neurosurgeons have resorted to the technique of locating the tumor with reference to prominent cranial features, such as the locations of the sockets for the ears, eyes and nose. Obviously such "landmarks" are inadequate for the task of locating a tumor that may be less than 5-mm in diameter. So in practice, CT scan data has been very useful for diagnosis, but much less useful for surgery. This is particularly so because while CT scan data may be used to determine X and Y coordinates with accuracy, it is more difficult to determine the Z coordinate due to the lack of a precise base line for the first slice of the scan. A beam of light on the scalp, or calculation of the orbitomeatal line are not accurate enough for use in determining the Z coordinate of a very small lesion.

Continued improvement in CT resolution may soon lead to the localization of an intracranial tumor too small to be located and removed by conventional methods. This possibility led the inventors of the present invention to consider stereotactic methods of dealing with minute lesions since no surgical method had previously been available for approaching accurately such small lesions. A stereotactic system using a tissue expander is described by C. Hunter Shelden, et al., in an application Ser. No. 797,843, filed May 17, 1977, now U.S. Pat. No. 4,386,602 titled "Intracranial Surgical Operative Apparatus." Briefly, a stereotactic guide mechanism is clamped on the patient's head for holding a micromanipulator fixed relative to the cranium. The stereotactic guide mechanism is clamped to an extension of the operating table and so adjusted as to place the micromanipulator in a position to hold a guide for surgical instruments at an appropriate angle in space for entry of the cranium in a straight line to the lesion. The angle of entry is selected by the neurosurgeon based upon such factors as the size, shape and location of the lesion, and specific areas of vital brain function to be avoided.

Once the stereotactic guide mechanism is properly aligned for the angle of entry, the guide on the micromanipulator is used during surgery to advance the necessary instruments. First a scalp incision is made down to the bone, and a burr hole is made through the skull and enlarged as necessary. Next a dural incision is made and a small dilating probe is inserted which gradually displaces the brain tissue along the guided straight line to the depth of the target point (tumor). Other probes of successively larger diameter are inserted to expand the passageway sufficiently to allow easy insertion of an 8-mm tumorscope, a hollow probe with expandable tulip-like blades at the tip. After initial entry to the depth of the lesion, the blades at the tip are expanded by an inner tubular sleeve which, when moved distally, separates the blades to open the tip of the probe. When fully opened, the diameter of the circular opening across the tip is 6 mm. Opening the blades expands the surrounding tissue with sufficient stretch to prevent bleeding into the air-filled cavity created by the expanding blades. The tubular sleeve of the probe provides a 5-mm channel through which surgical instruments may be inserted, such as a stereo endoscope with xenon arc illumination, and a radiation tracer probe. A rotary extractor and other instruments necessary for the operation and removal of a tumor, or blood clot from a small intracerebral hemorrhage, are inserted through a lateral opening in the shaft of the scope. Thus, a micromanipulator for guiding the tactical instruments is, in turn, mounted on a stereotactic guide mechanism which accurately defines a passageway and maintains the straight line of approach at the desired angle of entry to the lesion which has been accurately located by the CT scan with reference to the cranium in three-dimensional coordinates.

The problem is to properly align the stereotactic guide mechanism so that the slide axis of the instrument guide passes through the center of the lesion, and to adjust the micromanipulator so that all of the probes, including the tumorscope with the expandable tip, can be inserted to just the precise depth. The angle and depth of entry cannot be accurately defined in a stereotactic guide mechanism with reference to cranial areas alone. At least not accurately enough for lesions of 5-mm or less.

OBJECTS AND SUMMARY OF THE INVENTION

An object of this invention is to provide a method and apparatus for the location of regions in a patient to be treated with a high degree of accuracy using three-dimensional coordinates.

Another object of the invention is to provide a method and apparatus for alignment of a stereotactic guide mechanism to guide instruments to the region to be treated using three-dimensional coordinates to the same degree of accuracy with which the region is located by CT scans.

These and other objects of the invention are achieved by fixing a reference ring on a patient prior to CT scanning with a reference plane (preferably its center plane) parallel to the scanning plane (i.e., perpendicular to a CT scan table). A base bracket secures the ring to an extension to the CT scan table. The position of the x-ray scan apparatus on the CT scan table establishes the position of a region to be treated in terms of a number of successive scans from a base line scan established with reference to the ring, thus defining the third of the three-dimensional coordinate system, namely the Z-axis of an X, Y and Z coordinate system. The X-axis is arbitrarily chosen to be in the plane of the ring and parallel to the table; the Y-axis is then in the plane of the ring and perpendicular to the table. This defines the center of the ring used to establish a reference (origin) for the Z axis which is perpendicular to the X and Y axes.

To facilitate establishing a precise origin for the coordinate system, three (and preferably four) major pins are positioned on the ring in a circle extend equally in the same direction normal to the reference plane. These pins thus define a circle, the center of which in turn defines the origin of X and Y coordinates for each CT scan, and the tips of these pins defines the origin of the Z axis because the length of the pins from the center plane of the ring is known. To facilitate establishing a precise base-line scan for the sequence of CT scans through the regions of interest, one or more sets of minor pins are placed in known positions relative to the major pins, and preferably on the circle defined by the major pins. The minor pins are of different lengths, the difference between any two pins of nearest equal length being about one millimeter in order to establish a base line for the CT scans that is known to within ½ mm. In practice, the ring is preferably positioned so that the tips of the minor pins will all be to the side of the ring on which the regions of interest are located. CT scans are then made along the Z-axis across the lengths of the major and minor pins and through the regions of interest.

In processing the scan data, the center of the circle is first computed. Where major pins are provide, this is done by determining the center of each major pin and constructing a circle that passes through all major pins. The parameters of the circle thus determined are in CT scan pixel coordinates, namely $(x-a)^2+(y-b)^2=r^2$, where $(a,b)$ is the center of the circle, and r is the radius. The actual X and Y ring coordinates can then be computed for any given point in the ring from the equations, $X=q(x-a)$; $Y=q(y-b)$, where $(x,y)$ is the given point in pixel coordinates, q is the pixel size. The Z coordinate is then determined from the depth of scan using the center plane of the ring as the reference. Where the minor set, or sets of pins are provided, the number of pins located is noted for each scan. When the pin count changes between consecutive scans, the Z coordinate for the last scan is estimated as the average height of the shortest pin still appearing and of the pin just disappearing, plus half the height of the ring. This establishes a precise Z coordinate for this last scan to be used as the base line for subsequent scans, each scan being spaced a predetermined increment (such as 5-mm or 1.7-mm) along the Z axis, then adding the Z coordinate for the base-line scan and these increments to determine the Z coordinate of any subsequent CT scan.

To facilitate identifying the pins as to their height, the pins in each set are evenly spaced on the ring in order to height in a particular direction, such as counterclockwise from the tallest pin to the shortest. If the increment between the pins is 1-mm, the base-line scan coordinate is along the Z axis determined to within 0.5-mm. The Z-axis for any scan may thus be determined for any region of interest with an accuracy of 0.5-mm. It is only necessary to establish a base-line scan for the Z-axis, and then determine the scan depth to the region using the scale of the CT table for each subsequent scan out to the region. CT scan tables are provided with scales that are accurate to within the depth of each slice (e.g., 5-mm or less).

The center of or other point of a region of interest is visually identified in a CT scan display, and its X, Y and Z coordinates are calculated from the CT scan data. The X and Y coordinates are calculated by multiplying the difference in pixel coordinates from the center of the ring to the point or center of the region of interest by pixel size, and the Z coordinate is determined directly.

The coordinates of the point or center of the region of interest is transferred to a stereotactic test system comprised of: a standard ring on a test stand where the standard ring is identical to the ring on the patient, except without pins if pins are provided on the patient's ring; a sexton-like stereotactic guide mechanism attached to the standard ring using two pins and a bracket; a tumorscope-like probe; means for placing a phantom target in the test stand relative to the standard ring at the coordinates of the point or center of the region of the patient that is of interest; and a mechanism for directing the probe to the phantom target in the test stand at X, Y and Z coordinates from any direction within a hemisphere on one side of the ring. The stereotactic guide mechanism thus set up is then transferred from the standard ring to the ring fixed to the patient. Meantime the extension of the CT table to which the patient's ring is clamped is transferred with the patient to the operating room where it becomes an extension of the operating table.

To assist the surgeon in determining the location and best stereotactic approach to the point or center of the region of interest, image processing of CT-scan data may be employed which includes display of CT-scan data, using different colors for different pixel density ranges instead of shades of gray to better enable detection and location of all of the different physical elements in the scan, and a single pixel spot controlled as to its position by an observer to enter into a computer the pixel X and Y coordinates of chosen spots, such as the center and boundary of any element in the region of interest. From the data thus obtained from each of a series of CT scans in sequence, three-dimensional representations of each element are produced. Perspective views of these elements can be displayed using algorithms that calculate volumes, surface areas, positions and distances between all elements. By choosing multiple-view angles, a full three-dimensional shape of the lesion can be determined, thereby providing further important diagnostic and preoperative information. Further CT scan data processing gives valuable information for microanalysis of the element, such as enlargement to full screen size of a precise area, plus the steepness of the various surfaces or interfaces of the element and underlying edema contiguous to the element.

The novel features that are considered characteristic of this invention are set forth with particularity in the appended claims. The invention will best be understood from the following description of an exemplar when read in connection with the accompanying drawings.

Reference will now be made in detail to an exemplar of the invention, an example of which is illustrated in the accompanying drawings.

DESCRIPTION OF PREFERRED EMBODIMENTS

Figure 1:
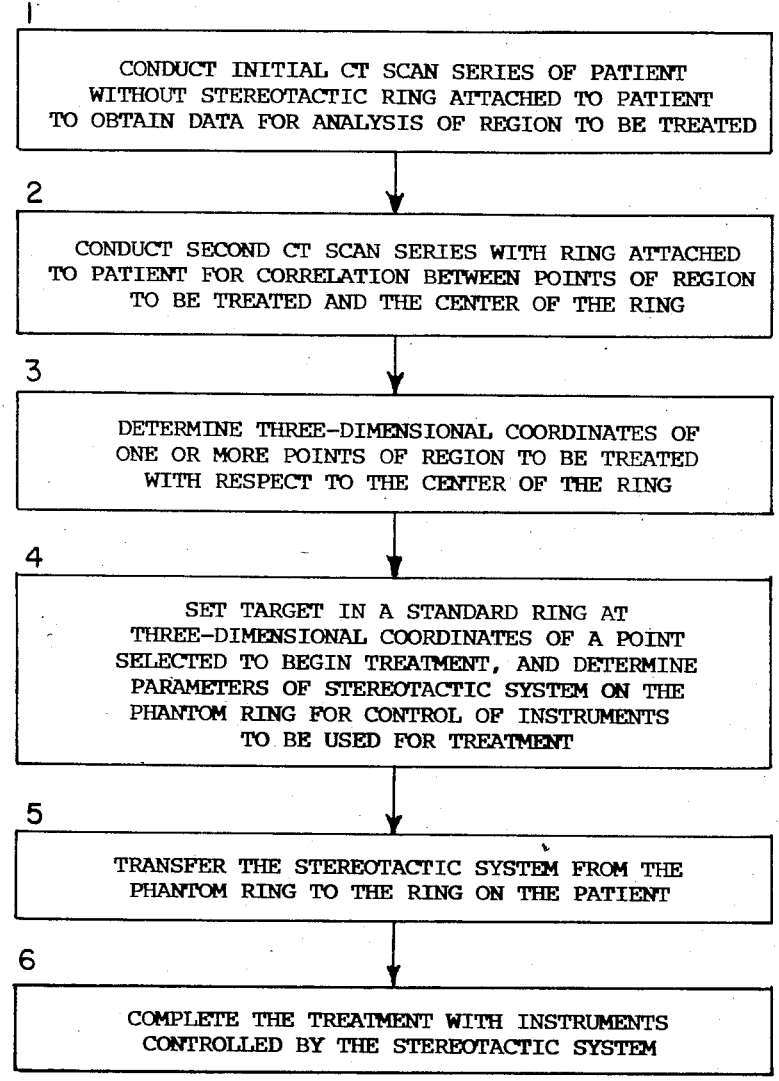
FIG. 1 presents a general outline of the protocol for neurosurgery using the novel stereotactic method and apparatus for the removal of minute intracranial or other lesions.

Referring now to FIG. 1, the novel stereotactic method of this invention is outlined for the treatment of large or small (less than 5-mm) intracranial lesions as an example. With the development and refinement of computerized tomography (CT), even small lesions can be detected by noninvasive (x-ray) scanning with computer processing of the data. For example, by using a General Electric CT/T 7800 tomography scanner with 5-mm scan slices and a PDP-1145 computer, data processing of various kinds is possible to determine not only the X and Y coordinates of a lesion, but also the Z coordinate. The coordinate system is defined with the positive X axis to the patient's right, and the positive Y axis to the patient's anterior. On a viewing screen, this appears as a positive X to the left and a positive Y up. The Z axis will only be positive, from a reference plane out to the lesion.

Figure 2:
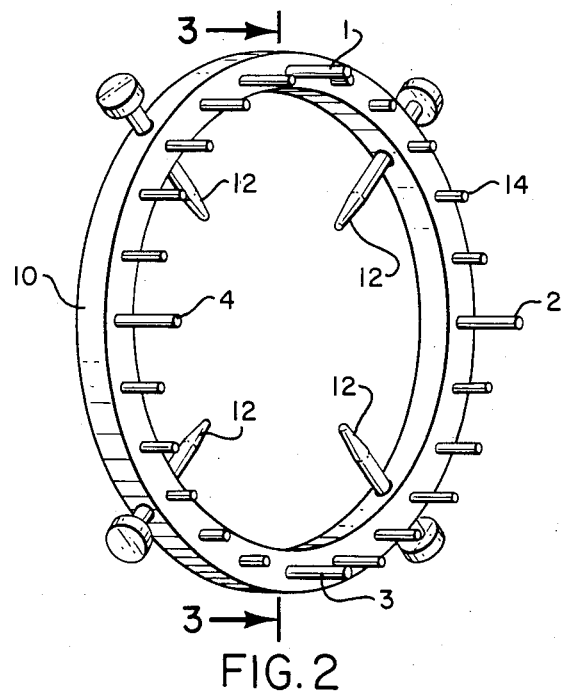
FIG. 2 shows a stereotactic ring having pins disposed in a circle for use in determining the X, Y and Z axes of a lesion from CT scan data.
Figure 3:
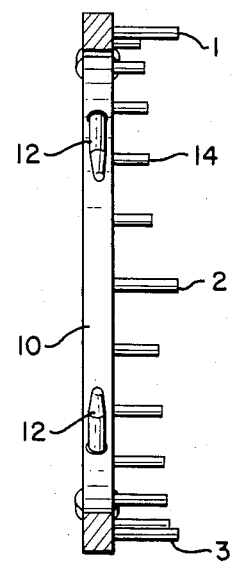
FIG. 3 is a sectional view of the ring in FIG. 2 taken on a line 2—2.
Figure 4:
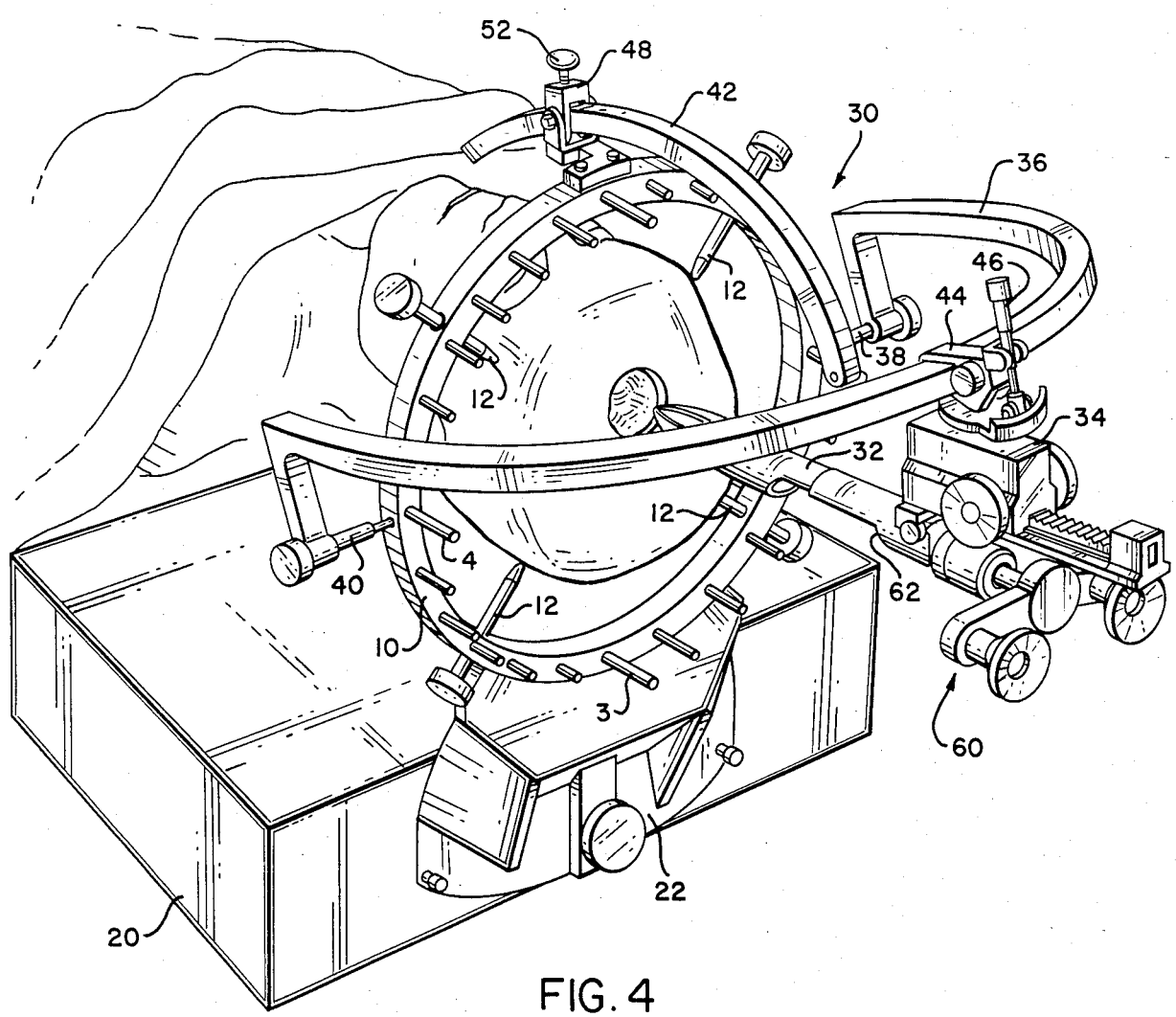
FIG. 4 is a perspective view of the ring in FIG. 2 attached to a patient's cranium for neurosurgery using a sexton-like stereotactic guide mechanism attached to the ring.

To establish the coordinates in a stereotactic system with the same accuracy for treatment, a stereotactic aluminum ring 10 shown in FIGS. 2 and 3 is attached to the patient using four skeletal attachment pins 12 as indicated in FIG. 4. Aluminum was selected to help minimize artifacts on the CT scans. Note that pins, such as pin 14, extend from the ring parallel to the axis of the ring (i.e., perpendicular to the plane of the ring), and that four longer pins (1, 2, 3 and 4) are positioned at cardinal points (i.e., 90° apart). The remaining pins (twenty in number) are equally spaced in two sets of ten pins, one set in each half of the ring, where the pins of a set vary in height by one millimeter from one pin to the next in a predetermined direction, such as clockwise, as more clearly shown in FIG. 3. These two sets of pins, referred to herein as minor pins, are used to aid in determining the Z-axis coordinate of a lesion with respect to the center plane of the ring. The four major pins at the cardinal points of the ring are used to aid in establishing the center of the ring from which the X and Y coordinates of a lesion are defined. These major pins may be 18 mm in length, and the longest of the minor pins may be, for example, 15 mm.

Before the stereotactic ring is attached, a complete CT scan is conducted as the first step in FIG. 1 to establish the general location of the lesion and to create three-dimensional views and analyses that establish the size, shape and relative orientation of the lesion to be treated. This is essential in determining the optimum point to start the process, in determining the pathway to the tumor or lesion to be treated that will minimize or eliminate damage to intervening structures, and to precisely determine the actual shape and volume to be treated. In addition, this analysis is essential to the later determination of all X, Y and Z coordinates controlling surgery for larger volumes where several coordinate points are needed to define all of the boundaries of the lesion.

In the second step, the stereotactic ring is placed on the patient's head for precise correlation between the location of the region to be treated and the control of an instrument to accurately treat that region. This is essential for determining all coordinate points to be reached by the treating instrument. After a second CT scan series that determines these pertinent coordinates with reference to the ring, the ring remains on the patient during treatment (surgical, adjuvant therapy or other treatment) in order that the apparatus to be used for treatment may be connected to it for proper orientation and guidance of the apparatus.

The base of the ring is mounted on an extension 20 of a CT scan table (not shown). This is preferably done by mounting the ring on the extension 20 of the CT scan table with a bracket 22 (as shown in FIG. 4) so that later the bracket and ring may be fastened to a similar extension of the operating table, or so that the extension 20 and bracket 22 may be transferred from the CT scan table to an operating table. In either case, the bracket mounts the ring perpendicular to the CT scan table in order that the Z coordinate to be determined be perpendicular to the center plane of the ring and parallel to the CT scan table. The X and Y coordinates will then be determined in the center plane parallel of the ring. The second CT scan series is then made through the region of interest and to the pins past the tips of the major pins and past the tips of at least some of the minor pins. In the G.E. 7800 tomography scanner, the scans (slices) are taken every 5-mm. In more recently developed equipment, slices as thin as 1.7-mm may be taken. In either case, the information for the stereotactic coordinates must be obtained from the CT scan data. The major problem is determination of the Z coordinate from the center plane of the ring, with an accuracy of one millimeter, or less.

The X and Y coordinates of the lesion with respect to the center of the ring can be determined from the scan data with an accuracy which depends only upon the pixel resolution of the data. The Z coordinate is more difficult because of a lack of a precise base line for the first slice of the scan. A beam of light on the scalp or calculation of the orbitomeatal line are not accurate enough for use in localizing very small lesions. Consequently, the stereotactic ring itself is used to establish a base line for the first slice.

Although the method to be described could be carried out by other processors and display devices for the CT scan data, the system which has been successfully used consists of a PDP-1145 computer, Tektronics 4010 terminal, COMPTAL frame buffer and monitors, a Tektronics graphics tablet, and a switch box to quickly and conveniently communicate with the computer in a more direct manner while using the tablet than is possible through the terminal. This processor and display system will be described more fully hereinafter with reference to FIG. 9.

The third step is to use this processor and display system, or an equivalent system, to obtain all X, Y and Z coordinates necessary for the processing volume to be treated, i.e., to obtain the X, Y and Z coordinates of the lesion relative to the center of the ring. Note that the three-dimensional image display of the lesion, skull and related structures, with enlargement of selected areas in the first step and the data of this step together assist the surgeon in determining the best angle of approach. Meantime, the patient is prepared for surgery without removing the stereotactic ring 10. The ring is attached to the operating table during surgery, preferably in the same perpendicular orientation with the table as with the CT scan table, although that is not essential because, as will become evident from the following description, the stereotactic system to be used during surgery is oriented relative to the ring, not the table. Attachment of the ring to the table is merely a matter of convenience, and to help immobilize the patient's head during surgery.

The major pins, which are positioned at 0°, 90°, 180° and 270° on the ring, are located in the CT scan data, such as with a tracking pin by the user. A conventional homing algorithm finds the exact centers of the major pins with a resolution of the pixel data, as follows:

$$x(\text{center}) = \frac{\sum_{v=y-w}^{y+w} \sum_{u=x-w}^{x+w} u \cdot D_{uv}^2}{\sum_{v=y-w}^{y+w} \sum_{u=x-w}^{x+w} D_{uv}^2} ; \quad (1)$$

$$y(\text{center}) = \frac{\sum_{v=y-w}^{y+w} \sum_{u=x-w}^{x+w} v \cdot D_{uv}^2}{\sum_{v=y-w}^{y+x} \sum_{u=x-w}^{x+w} D_{uv}^2}$$

here:
 D = the Density of the point (u,v) expressed as a non-negative number,
 W = the homing width used by the algorithm (currently 5),
 x = the x scan coordinate located by the tracking pen, and
 y = the y scan coordinate located by the tracking pen.

The equation of the circle of pins is then approximated in pixel coordinates from the equation of a circle, which is as follows:

$$(x-a)^2 + (y-b)^2 = r^2 \quad (2)$$

where (a,b) is the center of the circle, and r is the radius. Although three points define the equation of a circle, the fourth point is included to reduce statistical error. The parameters of the equation of the circle, a, b and r, are determined as follows:

$$a = \frac{1}{4} \sum_{p=1}^{4} x_p(\text{center}); \quad b = \frac{1}{4} \sum_{p=1}^{4} y_p(\text{center}) \quad (3)$$

$$r = \frac{1}{4} \sum_{p=1}^{4} \{[x_p(\text{center}) - a]^2 + [y_p(\text{center}) - b]^2\}^{\frac{1}{2}} \quad (4)$$

where: p = pin number 1,2,3, or 4 for 0°, 90°, 180° and 270°.

This estimation of the equation of the circle, based upon an estimate of the center of mass of the four cardinal points and the averaged radii from the center of mass to each point, is graphed on the Comtal display as a check and should pass through all of the pins of the ring. This equation is in pixel coordinates. To determine the coordinates of a point (i.e., the center of the tumor as located via a magnified image with the tracking pen) in ring coordinates (where point 0,0,0 is defined as the center of the ring in all three dimensions) the following conversion equations are used:

$$X = q(x-a); \quad Y = q(y-b) \quad (5)$$

where:
 (x,y) is a point located by the tracking pen in pixel coordinates,
 X and Y are the ring coordinates of this point, and
 q is the pixel size.

The X and Y coordinates of the lesion with respect to the center of the ring can thus be determined directly and accurately from CT scan data once the four major pins are located. Note that it is not necessary for the patient's head to be centered in the ring, and since the ring is not removed until after surgery, the origin (0,0,0) for the three axes will remain fixed relative to the lesion.

Determination of the Z coordinates is also made from CT scan data, preferably using the minor pins, but the accuracy of the Z coordinate is dependent upon the plane of the ring being parallel to the scanning plane, i.e., perpendicular to the CT scan table. This can be checked by displaying successive scans taken from a plane next to the ring out until the tips of the four major pins disappear from a CT scan display. The major pins should disappear from the displayed scans simultaneously. If not, an adjustment must be made until they do. A similar checking procedure may be followed using the minor pins, particularly if four sets of minor pins are provided, rather than two as illustrated.

In processing the scan data, the number of pins located on each scan is noted (i.e., entered into the computer). When the pin count between consecutive scans changes, the Z coordinate from the center of the ring to that scan is estimated as the average height of the shortest pin still appearing (or which disappeared) and the pin which disappeared (or is still appearing, depending on the direction chosen for the processing of the scan data). To this is added one-half the thickness of the ring. Since the increment between the pins is one millimeter, this locates a base-line scan with respect to the center plane of the ring along the Z axis with an accuracy of one-half millimeter. The Z coordinate of a lesion is then determined by counting the scan slices from the base line to the lesion, and adding the distance of the base line to the center plane of the ring. Next a tracking pen is used to locate the center of the lesion. The X and Y coordinates of that center are then calculated by multiplying the difference in pixel coordinates from the center of the ring to the center of the lesion by the pixel size. This completes determining the X, Y and Z coordinates of a lesion.

The purpose of determining the X, Y and Z coordinates with respect to the center of the ring is to be able to set up a very small target 24 (FIG. 5) on the end of a rod 26 at the exact position of the lesion, but with respect to a standard ring 28 to which is attached a stereotactic guide mechanism 30. The neurosurgeon can then determine the angle of approach to use and set up the stereotactic guide such that a tumorscope 32 can be guided to the target. A calibrated slide 34 is used to move the tumorscope in on the chosen pathway to the target. The pathway is chosen or set by adjustment of a sexton-like guide mechanism comprised of a calibrated semicircular yoke 36 on support pins 38 and 40 inserted into holes in the dummy ring, and calibrated sector 42. This guide mechanism is shown with the sector on top for convenience in the illustration. In practice, it could be inverted on the ring, depending upon the approach angle the surgeon chooses.

One end of the sector 42 is attached to the yoke 36 on a slide 44 having a control element 46 for locking the slide 44 on the yoke 36 at a particular angular position. The calibrated sector 42 passes through a block 48 pivoted on a support block 50 on top of the ring. The sector 42 may slide through the block 48 to raise or pivot the yoke 36 to a desired position, and then be locked in place by a set screw 52. Once all of these adjustments are made, the stereotactic guide mechanism 30 may be removed from the standard ring 28 and placed on the patient's ring 10 for surgery, as shown in FIG. 4. Only the slide 34 for the tumorscope is backed off during this transfer, but first its calibrated position is noted.

Figure 5:
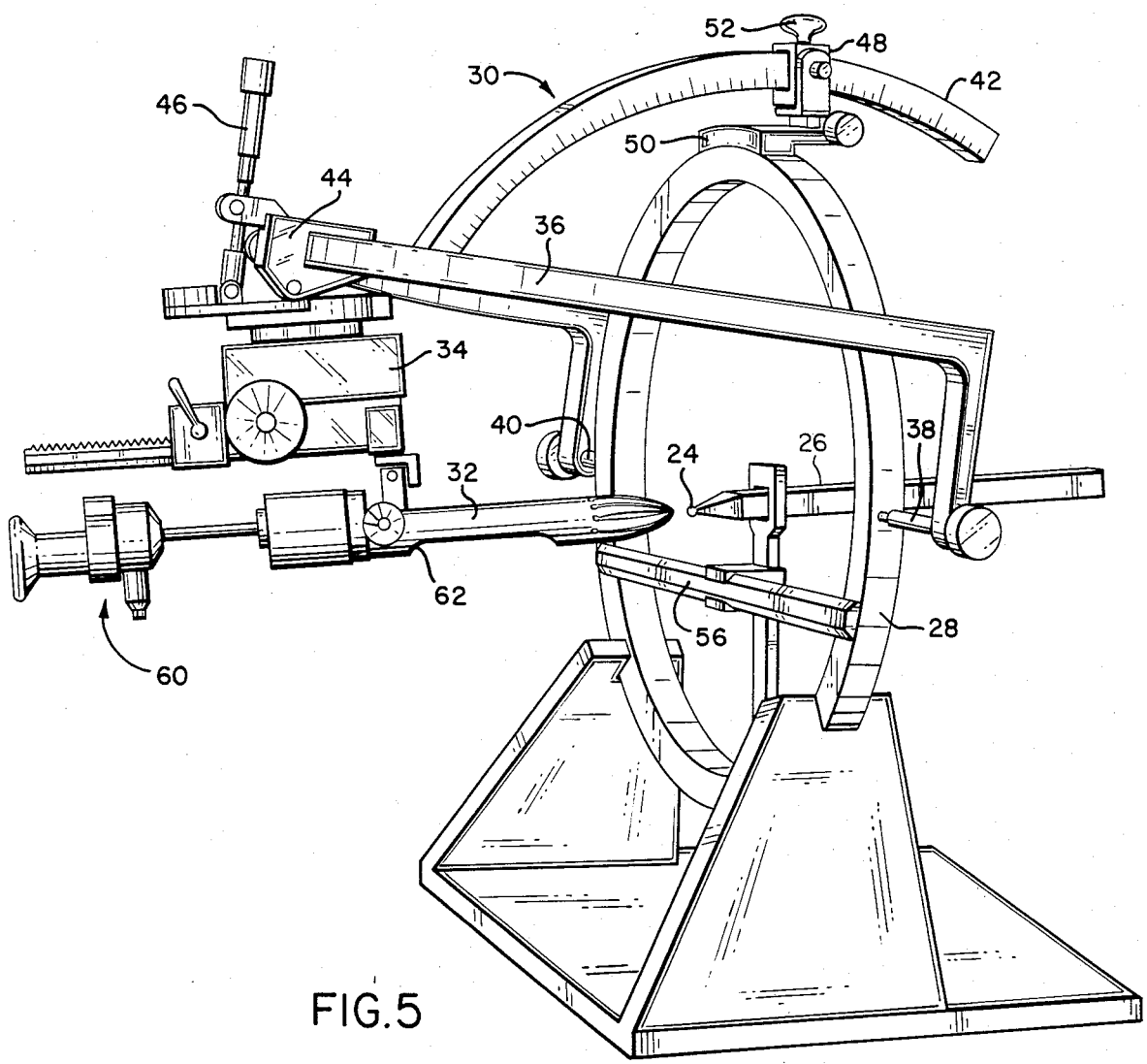
FIG. 5 illustrates the sexton-like stereotactic guide mechanism of FIG. 4 attached to a standard ring for setting up the desired angle of approach to a point corresponding to the three-dimensional (X, Y and Z) coordinates of a lesion in the patient's cranium relative to the center of the ring.

This procedure for setting up the stereotactic guide mechanism 30 is indicated as step 4 in FIG. 1 where the target refers to the target 24 on the rod 26 in FIG. 5. Note that the X and Y coordinates for the target are set by adjusting the position of a cross bar 54 on a horizontal bar 56. By adjusting the calibrated position of these bars, the Z axis defined by the rod is moved in the X and Y axes. That Z (rod) axis is perpendicular to the centerline plane of the ring. Moving the rod 26 itself relative to the bar 52 on which it is carried will then set the Z coordinate. Verniers are provided for the stereotactic X-, Y- and Z-axis scales as needed for the accuracy desired, such as one-half millimeter. It is thus possible to maintain the desired accuracy in setting up the stereotactic guide mechanism for the chosen attack angle, and in transferring the stereotactic guide mechanism to the ring on the patient's head. In that regard, although only one pair of holes for the pins 38 and 40 are indicated, in practice the patient's ring and the standard ring may have flat sides with sets of holes spaced vertically to permit the yoke 36 of the guide mechanism to be moved up or down as may be needed for a lesion near the front or back of the patient's head.

The tumorscope 32 is described in the aforesaid application Ser. No. 797,843, as well as tissue expanders which can be slidably inserted into the brain tissue through the tumorscope. Other instruments can be inserted in a similar way, such as a surgical knife, irrigation and suction apparatus and a binocular optical system. Illustrated in FIG. 5 is a binocular optical system 60 which permits the surgeon to look through the open tulip-like end of the tumorscope. Once it is withdrawn, some other instrument may be inserted in its place. Alternatively, while the optical system is still in place with its optical tube above the axis of the tumorscope, an instrument may be inserted through a side vent 62.

The orientation illustrated for the stereotactic mechanism in FIG. 4 and FIG. 5 is actually inverted to facilitate illustration and description. In practice, the system would be rotated on the rings 180° for the approach angle shown, thereby to pass the sector 42 through the bracket 22 and place the slide 34 above the yoke 36. This then puts the tumorscope 32 on top with the vent 62 up for ready access by the surgeon.

Once the stereotactic guide mechanism has been transferred from the standard ring in FIG. 5 to the ring on the patient's head in FIG. 4, which is step 5 in FIG. 1, the patient's scalp is marked for incision. Then the stereotactic guide mechanism is transferred back to the standard ring to check to see that none of the vernier settings have changed, i.e., to see that the slide 34 will advance the tumorscope to the target with the same vernier reading for the slide. Then the stereotactic guide mechanism is again transferred to the ring on the patient's head to complete the treatment (e.g. surgery) as the last step (6) in FIG. 1, using the necessary tactical instruments.

Figure 8:
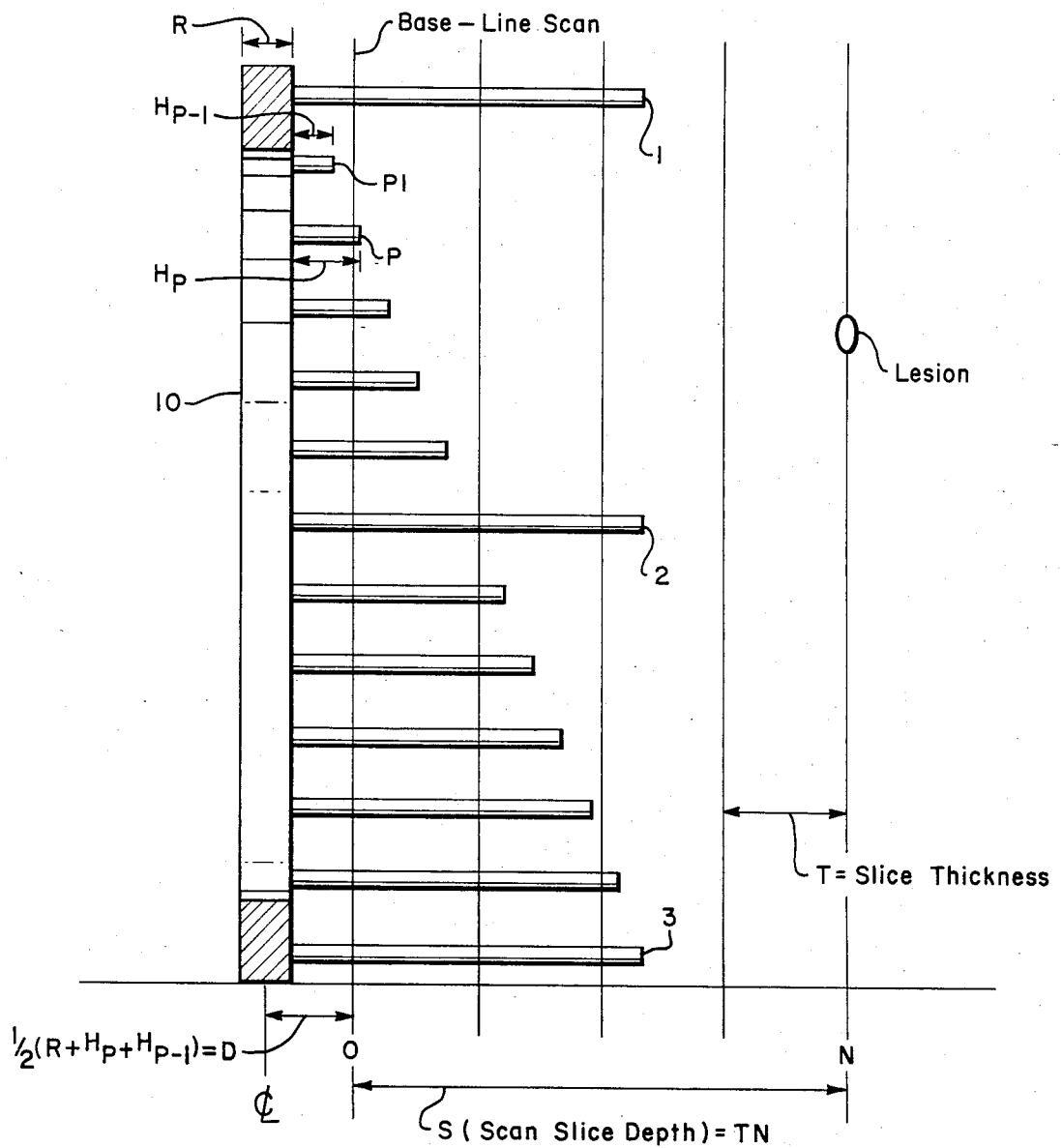
FIG. 8 illustrates schematically the manner in which the pins of the ring on the patient are used to determine the Z coordinate to a lesion.

Since the most difficult problem is determination of the Z axis coordinate because of a lack of a precise base line for slices of the scan (and the Z axis is determined essentially by counting slices from the base line to the lesion), the technique of using the minor pins for establishing the Z coordinate of a base line will now be described in more detail with reference to FIGS. 6, 7 and 8. However, it should be understood that, in the broadest aspects of the invention, the pins are not essential. For example, the base line could be established relative to the front edge of the ring, instead of the pins, particularly when the slice thickness is 1.7 mm or less.

Figures 6, 7:
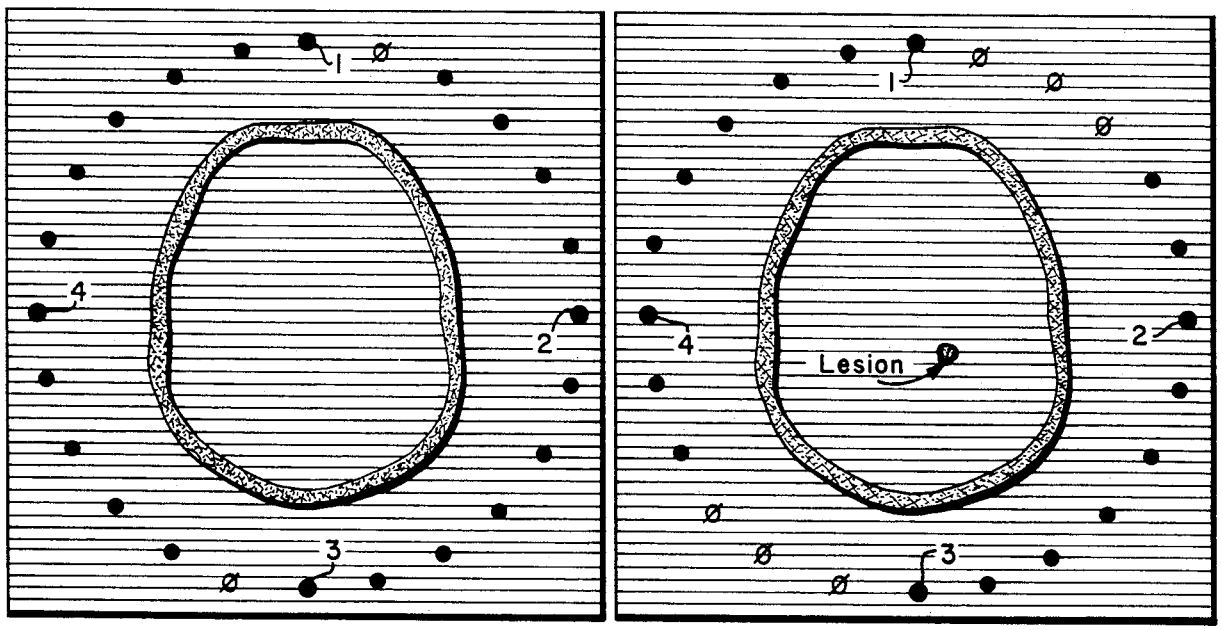
FIGS. 6 and 7 illustrate CT scan displays showing the pins of the ring from which the X and Y coordinates of a lesion are determined and, from additional scans, the Z coordinate as well

In FIG. 6 there is shown a scan in which the shortest pins at positions indicated by the symbol φ have just disappeared. It is assumed that a previous scan at a position closer to the ring clearly shows the shortest pins. Subsequent scans will cause successive pins to disappear, as shown in FIG. 7 where three of the pins of each set have disappeared. Any scan in which a pin has disappeared may be used as a base line since its distance (Z coordinate) from the center plane of the ring can be established by knowing the height of the pin of either set that disappeared and the next pin that still appears and the thickness of the ring. (Note that corresponding pins of each set should disappear at the same time if the ring is parallel to the CT scans.)

If a lesion appears within the field of the pins, as shown in FIG. 7, its Z coordinate could be determined directly. However, in the more usual case, the ring will be placed on the patient's head so that the lesion will appear in a scan slice beyond the field of the pins as shown in FIG. 8 where the base line scan to be used is indicated by the numeral 0, and the scan which includes the lesion is indicated as the Nth scan. The Z coordinate of the lesion is thus determined to be (TN+D) mm where D is the distance of the base-line scan from the centerline plane of the ring in millimeters, and T is the scan slice thickness, e.g., 5 mm (or 1.7 mm), or S+D, where S is the slice depth equal to slice thickness times the number of slices.

In determining the Z coordinate of a lesion within the field of the pins, the following equation may be employed without first explicitly determining a base line scan.

$$Z = \tfrac{1}{2}(R + H_p + H_{p-1} + T) \quad (6)$$

where
R = ring thickness,
$H_p$ = height of shortest pin visible,
$H_{p-1}$ = height of the next shortest pin not visible in a scan through the lesion, and
T = scan slice thickness.

The fraction ½ divides the ring thickness in half so that the origin for the Z axis is established at the center-line plane of the ring. It also divides the sum $H_p + H_{p-1}$ to obtain an average pin height so that the maximum error from this portion of the equation is one-half the distance between successive pins, which is 0.5 mm for 1 mm height intervals. And finally it divides the slice thickness by one-half to decrease any error due to the distance that the lesion is away from the slice center to a maximum of T/2 for a lesion actually located at the edge of the scan field instead of its center. This correction is important for 5-mm slices, and of course the maximum error T/2 is lessened as the slice thickness is decreased, such as for 1.7-mm slices. For 5-mm slices, the above equation gives a maximum theoretical error of $(H_p + H_{p-1})/2 + T/2$, which is 0.5 mm + 2.5 mm = 3 mm. For 1.7-mm slices, the error is reduced to 0.5 mm + 0.85 mm = 1.35 mm. The Z coordinate to any slice depth beyond a particular slice etablished as a base line using pins p and p−1 is then determined by simply adding the slice depth, S, to the distance, D, of the base-line scan to the center-line plane of the ring.

Once the Z axis of the lesion is determined, the stereotactic mechanism shown on the ring in FIG. 4 can be set up as described above with reference to FIG. 5. But first the neurosurgeon will want to determine from the initial scan series data the best angle of attack using a processor and display system shown in FIG. 9 to enhance regions of interest by magnification, three-dimensional reconstruction.

Figure 9:
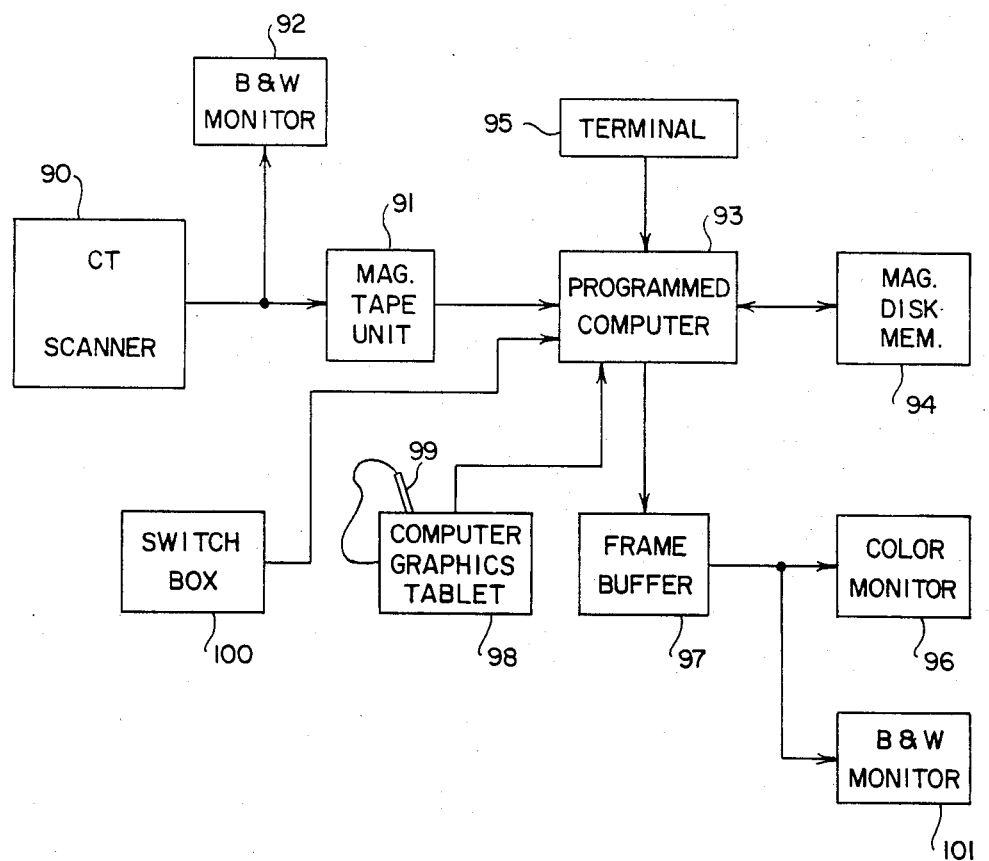
FIG. 9 illustrates a general block diagram of a computer-based image processing and display system for use in the method of FIG. 1.

Referring now to FIG. 9, a CT scanner 90, such as the General Electric 7800 (or a more recently developed model 8800 with 1.7-mm scan slices), provides image data which are decoded and first stored in a magnetic tape unit 91. A monitor 92, such as a Conrac black and white monitor, permits viewing the scan data as it is being developed and stored. The data is then transferred via a programmed computer 93, such as the Digital Equipment Corporation PDP 11/45, to a high speed magnetic disk memory 94 for more ready access during image analysis. Normally the computer and the rest of the system shown in FIG. 9 will be in a different location than the scanner 90, tape unit 91 and monitor 92, in which case the tape reels are simply carried to another magnetic tape unit at the location of the computer for transfer to the disk memory and subsequent analysis.

A terminal 95, such as a Tektronics 410 terminal, is used by the operator to command reading the data into the computer from the magnetic tape and storing it in the magnetic disk memory. It is also used to command all analysis and display operations as required. For example, the operator may command any sequence of scans to be displayed on a color monitor 96, such as a Comptal 8000, using a frame buffer 97, and he may command that the data of contours traced for each CT scan selected for display be stored in the computer for subsequent analysis and display, also controlled by the operator through the terminal.

Contours are traced on each scan with a computer graphics tablet 98, such as Tektronics 4953 graphics tablet, using a tracking stylus 99 on the tablet while the scan is being displayed on the monitor 96. The pen on the tablet causes a white pixel to be displayed on the monitor at the pixel coordinates of the stylus entered into the computer. At the same time, the computer stores the pixel data. To facilitate selecting and storing contour data, and other operations as well, a switch box 100 is preferably provided next to the tablet 98 so that the user may easily command the computer with his left hand while selecting and tracing contours with the right hand. For example, the switch box may be used to first just display the stylus position until it is in proper position to trace a contour. A flip of a switch will then command the computer to commence storing pixel data. Once the contour tracing is complete, the switch is returned to normal to stop storing data. All of the commands necessary for the computer could be entered through the terminal 95 using its general purpose keyboard, but it is preferred to provide special purpose (dedicated) command switches (or keys) on the switch box for operations to be carried out with the tablet to make it easier for the operator.

Any area having a traced contour may be redisplayed on the full screen for magnification by simply having each point of the area occupy a matrix of $N^2$ pixels, where N is an integer selected for the magnification desired. Contoured magnification of selected areas can be accomplished upon already magnified images by tracing selected contours and redisplaying a traced area. The magnification can be performed without filtering, which allows for very high magnification of minute areas of the image without blurring. In this manner, contour boundaries of small structures can be determined more accurately.

Using a black and white monitor 101, such as a Conrac monitor, the intensity map in the function memory of the frame buffer 97 may be manipulated, thus altering the gray scale mean and range. This provides optimal contrast for the viewing of structures within the image. Contrasts in the middle-to-white range are further enhanced by incorporating the gamma exponent correction for cathode ray displays onto the intensity map determined for the desired gray scale. In addition, a four color coding system may be selected for display on the color monitor independent of the gray scale to markedly extract CT density contrasts which are of diagnostic interest. This allows better detection of lesions and other structures than the conventional grey scale display technique, the detection of smaller lesions and structures, and more accurate determination of their boundaries.

For three-dimensional displays, a three-dimensional stack of all contours is constructed. Then the volumes of contours are computed and the surfaces between all contours are constructed and color coded. Also surface areas are computed. By choosing a viewer and light source positions, a shaded perspective view is then constructed using laws of perspective and reflectance. Hidden surfaces are eliminated and the resulting "three-dimensional" (perspective) image is displayed. This is done by using contour boundary data from discrete sets of points which are "tiled" together with triangular patches using the minimum surface area algorithm described by Fuchs, et al, in "Optimal surface reconstruction from plantar contours," University of Texas Technical Report 9, 1974. The computer (1) cuts the object space at the clipping planes in a manner described by I. E. Sutherland and G. W. Hodgman, "Reentrant polygon clipping," Commun Assoc Comput Machinery 17:32–42, 1974, (2) scales the objects in a manner described by W. Newman and R. F. Sproull, *Principles of Interactive Computer Graphics*, New York, McGraw-Hill, 1973, (3) performs a perspective transformation in a manner described by Sutherland, et al., infra, (4) calculates appropriate intensities for the object vertices as described by B. T. Phong, "Illumination for computer-generated images," University of Utah, 1973 (Ph D Thesis, Computer Science), (5) eliminates hidden surfaces as described by J. F. Blinn and M. E. Newell, "Texture and reflection in computer generated images," Comm Assoc Comput Machinery 19:542–547, 1976 and Newman, et al., supra, and (6) displays the resultant image on the color monitor 96. In addition, the clipping planes can be manipulated to cut away portions of an object and view internal structures, or individual objects can be extracted from their surroundings to be examined independently. By choosing multiple-view angles, the three-dimensional shapes can be studied, providing further important diagnostic and surgical information.

Calculation of the corrdinates of a lesion for surgery or other treatment is by an independent computer based analysis of the CT scan data stored in the magnetic disk memory. For that calculation, the data in the scan disk memory is displayed for each scan section in sequence to locate the tips of the major pins for the purpose of computing the center of the ring, and to locate the tips of minor pins for the purpose of determining the Z coordinate of a base-line scan from which the corrected Z coordinate of a lesion is computed.

Before computing the X, Y and Z coordinates of any desired point to be reached by an invasive process, the computer based analysis may be used to provide an algorithm that checks and corrects any errors either in the CT scan control or the CT scan computer indication of the Z axes position of scan sections it obtains and any possible misalignment of the plane of the head coordinate ring with the corresponding X, Y plane of the CT scanner. The ring device described above minimizes any chance for such misalignment. However, a check against an error in placement or malfunction of the CT scan motion, or its position data as transcibed for specific scan sections, is important to minimize any errors.

These check functions are performed as follows: The center of the coordinate system defining the X and Y coordinates of each scan section is computed as a specific pixel in the total pixel array as defined by its number in the total array of line and column numbers. Deviations of the specific pixel in different scan sections in sequence defines an angular variation from perfect alignment. This center pixel calculation is defined by the equations (1) through (4). A preliminary but not as precise a method for alignment check is as described above. That preliminary check is to monitor successive scan sections from a plane near the ring out until the tips of the major pins disappear from the display. If alignment is proper, they will disappear simultaneously.

The important aspects of the computer-based image process are:

(a) The initial display of serial scan densities by a four-color coding of a range of picture element (pixel) density quantized into four densities. This enables the better detection than the conventional grey scale display technique for the location of all of the regions of interest, including the case of brain tumors or lesions, the better detection of smaller regions and the more accurate determination of their boundaries.

(b) On these serial scans displayed on a color monitor, regions of interest are selected and their contours traced to enter into the computer the coordinates of the pixels thus traced, i.e., to enter the coordinates of the contours of the regions of interest, using a single pixel spot controlled by an observer through the computer graphics tablet.

(c) Construct from the required series of such contours from each serial scan over a region of interest a complete three-dimensional representation of each region.

(d) Display perspective views of these regions so reconstructed using a series of strategies for revealing hidden portions by either slicing away parts of the whole system or showing only selected elements of the whole system.

(e) Calculate volumes, surface areas, positions and distances between all regions of interest in such a three-dimensional reconstruction.

(f) Before computing the three-dimensional coordinates of any desired point to be reached by an invasive process, check and correct any errors either in the CT scan control or the CT scan computer indication of the Z axes position of serial scans and any possible misalignment of the plane of the head coordinate ring with the corresponding scan plane of the CT scanner. The ring mounting minimizes any chance for such misalignment. However, a check against an error in placement or malfunction of the CT scan patient mounting platform motion or its position data as transcribed to the computer data for specific serial scans is important to minimize any errors in this new, much more precise stereotactic method and apparatus for medical treatment.

These check functions are performed as follows: The center of the coordinate system defining the X, Y coordinates of each scan is computed as a specific pixel in the total pixel array as defined by its number in the total array of line and column numbers. Deviations of the specific pixel in different serial scans defines the angular variation from perfect alignment. This center pixel calculation is defined by the equations 2, 3 and 4. The alternate (but not as precise) method for alignment check using the tips of major pins as described hereinbefore is useful mainly for a preliminary on-line check prior to conducting a series of scans. It is not until after the scans are completed and the data are transferred to the magnetic disk memory for processing that this more precise check is made. Errors in both the initial Z axis positioning of the ring which is indicated as the zero value of Z, i.e., the center plane of the ring, is checked by comparing the CT scan table value of specific scans with the Z value determined from the data analysis procedures described hereinbefore. The difference should be only the average height of the two minor pins used for determining the Z coordinate of the base-line scan.

It should now be apparent that a stereotactic method and apparatus for treating a region of a patient's body has been described using CT scan data for initial visual analysis and calculation of coordinates for stereotactic treatment of a region of interest. The apparatus comprises at least a stereotactic ring affixed to the patient during CT scanning, and subsequently during treatment without removing, or otherwise moving the ring on the patient until after the treatment. Once the three-dimensional corrdinates are determined relative to the center of the ring using CT scan data, a stereotactic mechanism is set up on a standard ring supported by a stand with means for placing a target at the position defined by the three coordinates to assist selecting the pathway to the target and setting up the stereotactic mechanism to reach the target through the selected pathway. The stereotactic mechanism is then transferred to the ring on the patient. Processing of the CT scan data for initial visual analysis assists in selecting the region to be treated, and in determining the optimum angle of approach.

What is claimed is:

1. In a stereotactic system for treating a region of a patient's body, a method for using a tomography scanner for defining a selected point of the region in a three-dimensional coordinate system with reference to a predetermined point of means attached to the patient for establishing a reference point of said coordinate system for accurate control of instruments used to treat said region, comprising the steps of placing said means on the patient for precise correlation between the location of the region to be treated and the control system for treatment of the region in said three-dimensional coordinate system, conducting a series of parallel tomography scans through said region to be treated and at least part of said means for determination of three-dimensional coordinates of points in said region of the body of said patient to be treated relative to said reference point of said means, determining from data of said scan series three-dimensional coordinates with respect to said reference point of said means of at least one point of said region, determining all parameters of the system for control of instruments used for treatment with respect to said reference means, and completing the treatment with instruments guided by said control system with reference to said means still attached to said patient, wherein said reference means is a ring attached to the patient, and said reference point is the center thereof.

2. A method as defined in claim 1 wherein said ring is provided with a plurality of pins extending therefrom in one direction normal to the plane thereof, and said ring is mounted to be parallel to each tomographic scan, said pins extending in the direction of said region, and wherein said tomography scan includes scans through said pins to provide known points relative to the center of said ring for orientation of scan data in determining three-dimensional coordinates with reference to the center of said ring.

3. A method as defined by claim 2 wherein said pins are at least three at positions on said ring of equal radius from said reference center, whereby the coordinates of the center of the ring in two orthogonal axes in the plane of the ring may be computed from scan data by reference to the centers of said pins.

4. A method as defined in claim 3 including additional pins of different known heights, whereby the third coordinate of a base-line scan may be determined from the known heights of the tips of at least two pins, where one pin appears in successive scans and the other pin appears in one scan and disappears in an adjacent scan by adding to the height of the shortest pin half the difference in the known heights of the two pins, or subtracting from the longest pin half the difference in the known heights of the two pins, and a third coordinate for a point in the region to be treated is accurately determined by accumulating the spacing of successive scans of known spacing from said base-line scan to said point, and adding to the accumulated spacings of the scans the third coordinate of said base-line scan.

5. A method as defined in claim 4 wherein said additional pins are positioned on a circle which includes the pins used for establishing the coordinates of the center of the ring, and said additional pins are equally spaced and arranged in order of height, to facilitate identifying the addiional pins in displays of successive scans.

6. A method as defined in claim 5 wherein said additional pins are in sets, each set having a pin of known height diametrically opposite a pin of equal height.

7. A method as defined in claim 1, 2, 3, 4, 5 or 6 wherein the step of determining all control parameters of the system includes placing said control system on a standard ring similar to the ring on the patient, adjusting a target with respect to said standard ring at the coordinates of said one point selected for treatment, adjusting said control system for guidance of instruments to said target along a selected pathway, and transferring the system thus adjusted to said ring on the patient for stereotactic treatment.

8. In a stereotactic system for treating a region of a patient's body reached through a selected pathway to a point in the region using a three-dimensional coordinate system with reference to a ring attached to the patient for establishing a reference point for the three-dimensional coordinate system at the center of said ring, said ring having a plurality of pins of known heights from a plane in said ring, at least some of which differ in height by a known increment and at least three of which are spaced apart at equal radius from the center of said ring, a method of determining three-dimensional coordinates of a point in said region of the patient comprising the steps of making a series of parallel tomography scans at equal increments of spacing along the axis of said ring, said series extending through said region and at least some of said pins, including said pins at equal radius from said ring center, displaying said scans and from said scan displays, determining the centers of said pins of equal radius from said ring center, and determining the position of the center in said series of scans as a reference for two-dimensional coordinates in a plane of said ring relative to said ring, identifying two adjacent scans from said scan displays where two pins of heights that differ by a known increment appear in one scan and only one of said two pins appears in the adjacent scan, and computing the coordinate of one of said scans to be used as a base-line scan from said plane of said ring along the axis of said ring as the height of one of said pins adjusted by half the incremental difference in height of said two pins, identifying a scan that includes said point from said scan displays, and determining the third coordinate of said scan that includes said point as the sum of the coordinate of said base-line scan, and the number of equal scan increments from said base-line scan to the scan that includes said point, and determining the remaining two coordinates of said point relative to said reference point at the center of said ring.

9. In a stereotactic system as defined in claim 8 wherein said pins of equal height are spaced around said ring to define a circle, further including the method of checking that the ring is parallel to the scans by observing displays of a series of scans past the end of said pins of equal length to see that all pins of equal length disappear in the display at the same time.

* * * * *